(12) United States Patent
Alvarez et al.

(10) Patent No.: US 9,775,969 B2
(45) Date of Patent: Oct. 3, 2017

(54) REENTRY CATHETER AND METHOD THEREOF

(71) Applicant: The Spectranetics Corporation, Colorado Springs, CO (US)

(72) Inventors: Jeffery B. Alvarez, Redwood City, CA (US); David S. Nevrla, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

(21) Appl. No.: 14/631,592

(22) Filed: Feb. 25, 2015

(65) Prior Publication Data

US 2015/0165163 A1 Jun. 18, 2015

Related U.S. Application Data

(63) Continuation of application No. 13/229,392, filed on Sep. 9, 2011, now Pat. No. 8,998,936.

(60) Provisional application No. 61/503,477, filed on Jun. 30, 2011.

(51) Int. Cl.
*A61M 25/01* (2006.01)
*A61M 25/00* (2006.01)
*A61B 17/22* (2006.01)

(52) U.S. Cl.
CPC ............ *A61M 25/0194* (2013.01); *A61B 2017/22095* (2013.01); *A61M 25/0138* (2013.01); *A61M 2025/0058* (2013.01); *A61M 2025/0096* (2013.01); *A61M 2025/0183* (2013.01); *A61M 2025/0197* (2013.01)

(58) Field of Classification Search
CPC .......... A61M 25/0023; A61M 25/0032; A61M 25/0054; A61M 25/0138; A61M 25/0194; A61M 2025/0197; A61M 2025/0063; A61B 2017/22095; A61B 17/3209; A61B 2017/3454
See application file for complete search history.

(56) References Cited

U.S. PATENT DOCUMENTS

| | | |
|---|---|---|
| 3,853,004 A | 12/1974 | Cebuliak et al. |
| 4,227,293 A | 10/1980 | Taylor |
| 4,552,554 A | 11/1985 | Gould et al. |
| 4,664,112 A | 5/1987 | Kensey et al. |
| 4,712,547 A | 12/1987 | Bonnet |
| 4,774,949 A | 10/1988 | Fogarty |

(Continued)

FOREIGN PATENT DOCUMENTS

| | | |
|---|---|---|
| EP | 0166212 A2 | 1/1986 |
| JP | 2006181370 A | 7/2006 |

(Continued)

OTHER PUBLICATIONS

Belli et al., "Peripheral Vascular Occlusions: Mechanical Recanalization with a Metal Laser Probe after Guide Wire Dissection," Radiology, vol. 176, No. 2, pp. 539-541, Aug. 1990.

(Continued)

*Primary Examiner* — Sarah W Aleman
(74) *Attorney, Agent, or Firm* — Faegre Baker Daniels LLP

(57) ABSTRACT

The invention generally relates to method and apparatus for crossing an obstruction in a tubular member, and more particularly to a medical device method for crossing of a chronic occlusion in a subintimal or interstitial space of an artery.

20 Claims, 11 Drawing Sheets

(56) References Cited

U.S. PATENT DOCUMENTS

| | | | |
|---|---|---|---|
| 4,784,636 | A | 11/1988 | Rydell |
| 4,926,858 | A | 5/1990 | Gifford et al. |
| 4,994,067 | A | 2/1991 | Summers |
| 5,047,040 | A | 9/1991 | Simpson et al. |
| 5,053,044 | A | 10/1991 | Mueller et al. |
| 5,066,288 | A | 11/1991 | Deniega et al. |
| 5,092,872 | A | 3/1992 | Segalowitz |
| 5,100,426 | A | 3/1992 | Nixon |
| 5,104,382 | A | 4/1992 | Brinkerhoff et al. |
| 5,135,531 | A | 8/1992 | Shiber |
| 5,234,450 | A | 8/1993 | Segalowitz |
| 5,242,461 | A | 9/1993 | Kortenbach et al. |
| 5,279,551 | A | 1/1994 | James |
| 5,287,861 | A | 2/1994 | Wilk |
| 5,308,354 | A | 5/1994 | Zacca et al. |
| 5,334,211 | A | 8/1994 | Shiber |
| 5,336,176 | A | 8/1994 | Yoon |
| 5,391,177 | A | 2/1995 | Schwartz |
| 5,409,019 | A | 4/1995 | Wilk |
| 5,413,581 | A * | 5/1995 | Goy ................ A61M 25/01 604/102.01 |
| 5,423,846 | A | 6/1995 | Fischell |
| 5,429,497 | A | 7/1995 | Yamada et al. |
| 5,443,443 | A | 8/1995 | Shiber |
| 5,443,497 | A | 8/1995 | Venbrux |
| 5,512,044 | A | 4/1996 | Duer |
| 5,536,251 | A | 7/1996 | Evard et al. |
| 5,558,665 | A | 9/1996 | Kieturakis |
| 5,596,990 | A | 1/1997 | Yock et al. |
| 5,601,588 | A | 2/1997 | Tonomura et al. |
| 5,628,761 | A | 5/1997 | Rizik |
| 5,632,755 | A | 5/1997 | Nordgren et al. |
| 5,643,298 | A | 7/1997 | Nordgren et al. |
| 5,649,941 | A | 7/1997 | Lary |
| 5,651,781 | A | 7/1997 | Grace |
| 5,690,664 | A | 11/1997 | Sauer et al. |
| 5,695,469 | A | 12/1997 | Segal |
| 5,702,390 | A | 12/1997 | Austin et al. |
| 5,724,977 | A | 3/1998 | Yock et al. |
| 5,728,129 | A | 3/1998 | Summers |
| 5,746,758 | A | 5/1998 | Nordgren et al. |
| 5,776,154 | A | 7/1998 | Taylor et al. |
| 5,830,222 | A | 11/1998 | Makower |
| 5,836,868 | A | 11/1998 | Ressemann et al. |
| 5,841,893 | A | 11/1998 | Ishikawa et al. |
| 5,879,305 | A | 3/1999 | Yock et al. |
| 5,902,263 | A | 5/1999 | Patterson et al. |
| 5,935,108 | A | 8/1999 | Katoh et al. |
| 5,938,671 | A | 8/1999 | Katoh et al. |
| 5,941,893 | A | 8/1999 | Saadat |
| 5,951,567 | A | 9/1999 | Javier et al. |
| 5,972,019 | A | 10/1999 | Engelson et al. |
| 6,024,730 | A * | 2/2000 | Pagan ............... A61M 25/0054 604/264 |
| 6,027,514 | A | 2/2000 | Stine et al. |
| 6,066,149 | A | 5/2000 | Samson et al. |
| 6,080,171 | A | 6/2000 | Keith et al. |
| 6,080,175 | A | 6/2000 | Hogendijk |
| 6,081,738 | A | 6/2000 | Hinohara et al. |
| 6,096,054 | A | 8/2000 | Wyzgala et al. |
| 6,155,264 | A | 12/2000 | Ressemann et al. |
| 6,190,353 | B1 | 2/2001 | Makower et al. |
| 6,196,230 | B1 | 3/2001 | Hall et al. |
| 6,217,527 | B1 | 4/2001 | Selmon et al. |
| 6,221,049 | B1 | 4/2001 | Selmon et al. |
| 6,231,546 | B1 | 5/2001 | Milo et al. |
| 6,235,000 | B1 | 5/2001 | Milo et al. |
| 6,238,406 | B1 | 5/2001 | Ellis et al. |
| 6,302,875 | B1 | 10/2001 | Makower et al. |
| 6,402,778 | B2 | 6/2002 | Wang |
| 6,419,659 | B1 | 7/2002 | Phelps et al. |
| 6,419,685 | B2 | 7/2002 | Di Caprio et al. |
| 6,432,129 | B2 | 8/2002 | DiCaprio |
| 6,475,226 | B1 * | 11/2002 | Belef ................ A61B 1/3137 606/170 |
| 6,488,693 | B2 | 12/2002 | Gannoe et al. |
| 6,506,178 | B1 | 1/2003 | Schubart et al. |
| 6,506,200 | B1 | 1/2003 | Chin |
| 6,506,201 | B2 | 1/2003 | Di Caprio et al. |
| 6,511,458 | B2 | 1/2003 | Milo et al. |
| 6,533,753 | B1 | 3/2003 | Haarstad et al. |
| 6,533,755 | B2 | 3/2003 | Adams |
| 6,544,230 | B1 | 4/2003 | Flaherty et al. |
| 6,569,129 | B1 | 5/2003 | Holmes et al. |
| 6,579,302 | B2 | 6/2003 | Duerig et al. |
| 6,589,274 | B2 | 7/2003 | Stiger et al. |
| 6,592,568 | B2 | 7/2003 | Campbell |
| 6,596,005 | B1 | 7/2003 | Kanz et al. |
| 6,602,225 | B2 | 8/2003 | Eidenschink et al. |
| 6,655,386 | B1 | 12/2003 | Makower et al. |
| 6,663,577 | B2 * | 12/2003 | Jen ................ A61B 17/3207 600/585 |
| 6,676,667 | B2 | 1/2004 | Mareiro et al. |
| 6,702,777 | B2 | 3/2004 | Haim et al. |
| 6,719,725 | B2 | 4/2004 | Milo et al. |
| 6,736,841 | B2 | 5/2004 | Musbach et al. |
| 6,796,963 | B2 | 9/2004 | Carpenter et al. |
| 6,808,531 | B2 | 10/2004 | Lafontaine et al. |
| 6,818,001 | B2 | 11/2004 | Wulfman et al. |
| 6,881,216 | B2 | 4/2005 | Di Caprio et al. |
| 6,890,348 | B2 | 5/2005 | Sydney et al. |
| 6,923,827 | B2 | 8/2005 | Campbell et al. |
| 6,942,681 | B2 | 9/2005 | Johnson |
| 7,004,173 | B2 | 2/2006 | Sparks et al. |
| 7,056,323 | B2 | 6/2006 | Mareiro et al. |
| 7,083,639 | B2 | 8/2006 | Guinan et al. |
| 7,137,990 | B2 | 11/2006 | Hebert et al. |
| 7,147,655 | B2 | 12/2006 | Chermoni |
| 7,172,575 | B2 | 2/2007 | El-Nounou et al. |
| 7,172,621 | B2 | 2/2007 | Theron |
| 7,175,607 | B2 | 2/2007 | Lim et al. |
| 7,179,270 | B2 | 2/2007 | Makower |
| 7,201,770 | B2 | 4/2007 | Johnson et al. |
| 7,226,472 | B2 | 6/2007 | Pederson et al. |
| 7,273,485 | B2 | 9/2007 | Simpson et al. |
| 7,314,588 | B2 | 1/2008 | Blankenship |
| 7,329,267 | B2 | 2/2008 | Weber |
| 7,344,557 | B2 | 3/2008 | Yadin |
| 7,399,291 | B2 | 7/2008 | Vo et al. |
| 7,476,214 | B2 | 1/2009 | Sydney et al. |
| 7,553,324 | B2 | 6/2009 | Andreas et al. |
| 7,572,270 | B2 | 8/2009 | Johnson |
| 7,604,621 | B2 | 10/2009 | Eidenschink |
| 7,632,288 | B2 | 12/2009 | Wu |
| 7,951,186 | B2 * | 5/2011 | Eidenschink ......... A61L 29/146 623/1.11 |
| 8,956,376 | B2 | 2/2015 | Alvarez et al. |
| 8,998,936 | B2 | 4/2015 | Alvarez et al. |
| 2001/0000041 | A1 * | 3/2001 | Selmon ............... A61B 17/3207 600/585 |
| 2001/0014821 | A1 | 8/2001 | Juman et al. |
| 2001/0029387 | A1 | 10/2001 | Wolf et al. |
| 2001/0031981 | A1 | 10/2001 | Evans et al. |
| 2001/0034547 | A1 | 10/2001 | Hall et al. |
| 2002/0103459 | A1 | 8/2002 | Sparks et al. |
| 2003/0014100 | A1 | 1/2003 | Maria Meens et al. |
| 2003/0032999 | A1 | 2/2003 | Huang |
| 2003/0109809 | A1 | 6/2003 | Jen et al. |
| 2003/0171799 | A1 | 9/2003 | Lee et al. |
| 2003/0236542 | A1 | 12/2003 | Makower |
| 2004/0044392 | A1 | 3/2004 | Von Oepen |
| 2004/0170782 | A1 | 9/2004 | Wang et al. |
| 2004/0181252 | A1 | 9/2004 | Boyle et al. |
| 2004/0230219 | A1 | 11/2004 | Roucher |
| 2005/0004649 | A1 | 1/2005 | Mistry et al. |
| 2005/0021002 | A1 | 1/2005 | Deckman et al. |
| 2005/0027248 | A1 | 2/2005 | Suzuki et al. |
| 2005/0038382 | A1 | 2/2005 | Miller et al. |
| 2005/0049574 | A1 | 3/2005 | Petrick et al. |
| 2005/0049672 | A1 | 3/2005 | Murphy |
| 2005/0055078 | A1 | 3/2005 | Campbell |
| 2005/0059938 | A1 | 3/2005 | Malisch |
| 2005/0075711 | A1 | 4/2005 | Neary |
| 2005/0085845 | A1 | 4/2005 | Hilaire et al. |

(56) References Cited

U.S. PATENT DOCUMENTS

| | | |
|---|---|---|
| 2005/0085889 A1 | 4/2005 | Sundar |
| 2005/0090853 A1 | 4/2005 | Duchamp |
| 2005/0090888 A1 | 4/2005 | Hines et al. |
| 2005/0096722 A1 | 5/2005 | Lootz et al. |
| 2005/0102020 A1 | 5/2005 | Grayzel et al. |
| 2005/0107819 A1 | 5/2005 | Sater |
| 2005/0118370 A1 | 6/2005 | Varma et al. |
| 2005/0119731 A1 | 6/2005 | Brucker et al. |
| 2005/0131444 A1 | 6/2005 | Ricci |
| 2005/0171478 A1 | 8/2005 | Selmon et al. |
| 2005/0209559 A1 | 9/2005 | Thornton et al. |
| 2005/0271844 A1 | 12/2005 | Mapes et al. |
| 2005/0273021 A1 | 12/2005 | Burgermeister |
| 2005/0273149 A1 | 12/2005 | Tran et al. |
| 2005/0273153 A1 | 12/2005 | Clerc et al. |
| 2005/0277979 A1 | 12/2005 | Dorros et al. |
| 2005/0278011 A1 | 12/2005 | Peckham |
| 2005/0288629 A1 | 12/2005 | Kunis |
| 2006/0009737 A1 | 1/2006 | Whiting et al. |
| 2006/0009832 A1 | 1/2006 | Fisher |
| 2006/0015133 A1 | 1/2006 | Grayzel et al. |
| 2006/0025843 A1 | 2/2006 | Gurm et al. |
| 2006/0030922 A1 | 2/2006 | Dolan |
| 2006/0030924 A1 | 2/2006 | Van Der Leest et al. |
| 2006/0047336 A1 | 3/2006 | Gale et al. |
| 2006/0074476 A1 | 4/2006 | Holman et al. |
| 2006/0085058 A1 | 4/2006 | Rosenthal et al. |
| 2006/0106448 A1 | 5/2006 | Shaked |
| 2006/0129179 A1 | 6/2006 | Weber et al. |
| 2006/0135909 A1 | 6/2006 | Holman et al. |
| 2006/0173440 A1 | 8/2006 | Lamson et al. |
| 2006/0184186 A1 | 8/2006 | Noone |
| 2006/0235458 A1* | 10/2006 | Belson ............. A61M 25/0032 606/191 |
| 2006/0276749 A1 | 12/2006 | Selmon et al. |
| 2007/0021685 A1 | 1/2007 | Oepen et al. |
| 2007/0093780 A1 | 4/2007 | Kugler et al. |
| 2007/0208368 A1 | 9/2007 | Katoh et al. |
| 2007/0250036 A1 | 10/2007 | Volk et al. |
| 2007/0265563 A1 | 11/2007 | Heuser |
| 2007/0276419 A1 | 11/2007 | Rosenthal |
| 2008/0097247 A1 | 4/2008 | Eskuri |
| 2008/0114390 A1 | 5/2008 | Guinan |
| 2008/0125748 A1 | 5/2008 | Patel |
| 2008/0140101 A1 | 6/2008 | Carley et al. |
| 2008/0154172 A1* | 6/2008 | Mauch .................... A61F 2/82 604/164.13 |
| 2008/0228171 A1 | 9/2008 | Kugler et al. |
| 2008/0234717 A1 | 9/2008 | Bruszewski |
| 2008/0243065 A1 | 10/2008 | Rottenberg et al. |
| 2008/0243067 A1 | 10/2008 | Rottenberg et al. |
| 2008/0249465 A1 | 10/2008 | Ryder et al. |
| 2009/0088685 A1 | 4/2009 | Kugler et al. |
| 2009/0093829 A1 | 4/2009 | Melsheimer et al. |
| 2009/0124857 A1 | 5/2009 | Viola |
| 2009/0171430 A1 | 7/2009 | Baim et al. |
| 2009/0209910 A1 | 8/2009 | Kugler et al. |
| 2009/0234378 A1 | 9/2009 | Escudero et al. |
| 2009/0270888 A1 | 10/2009 | Patel et al. |
| 2010/0063534 A1 | 3/2010 | Kugler et al. |
| 2010/0286626 A1 | 11/2010 | Petersen et al. |
| 2010/0317973 A1 | 12/2010 | Nita |
| 2013/0006167 A1 | 1/2013 | Alvarez et al. |
| 2014/0371718 A1 | 12/2014 | Alvarez et al. |
| 2015/0119910 A1 | 4/2015 | Alvarez et al. |

FOREIGN PATENT DOCUMENTS

| | | |
|---|---|---|
| WO | 9713463 A1 | 4/1997 |
| WO | 9713471 A1 | 4/1997 |
| WO | 2008005888 A2 | 1/2008 |
| WO | 2013003757 A2 | 1/2013 |

OTHER PUBLICATIONS

Bolia et al., "Percutaneous Extraluminal (Subintimal) Recanalization of a Brachial Artery Occlusion Following Cardiac Catheterization," Cardiovascular and Interventional Radiology, vol. 19, pp. 184-186, 1996.

Bolia et al., "Percutaneous Transluminal Angioplasty of Occlusions of the Femoral and Popliteal Arterles by Subintimal Dissection," Cardiovascular and Interventional Radiology, vol. 13, pp. 357-363, 1990.

Bolia et al., "Recanalisation of Femora-Popliteal Occlusions: Improving Success Rate by Subintimal Recanalisation," correspondence to the editor, Clinical Radiology, vol. 40, No. 3, p. 325, May 1989.

Bolia et al., "Recanalization of Iliac Artery Occlusion by Subintimal Using the Ipsilateral and the Contralateral Approach," Clinical Radiology, vol. 52, pp. 684-687, 1997.

Bolia et al., "Subintimal and Intraluminal Recanalisation of Occluded Crural Arteries by Percutaneous Balloon Angioplasty," European Journal of Vascular Surgery, vol. 8, pp. 214-219, 1994.

Braun, "Guide Wire-assisted Placement of Non-End-Hole Nasoenteric Feeding Tubes," Radiology, p. 606, Feb. 2000.

Glasby et al., "Subintimal angioplasty," C212, 2008, vol. VI(1), pp. 12-16.

Heenan et al., "Clinics in Interventional Radiology: Percutaneous Transluminal Angioplasty by a Retrograde Subintimal Transpopliteal Approach," Clinical Radiology, vol. 49, pp. 824-828, 1994.

International Search Report and Written Opinion issued in PCT/US2012/052858 mailed Jan. 25, 2013 10 pages.

International Search Report and Written Opinion issued in PCT/US2012/045011 mailed Jan. 7, 2013, 10 pages.

International Search Report and Written Opinion issued in PCT/US2012/052852 mailed Nov. 2, 2012, 8 pages.

Mathis et al., "Use of a Guide Catheter as a Temporary Stent during Microcatheter Intervention," American Journal of Neuroradiology, vol. 19, pp. 932-933, may 1998.

Miyayama et al., "Use of a Catheter with a Large Side Hole for Selective Catheterization of the Inferior Phrenic Artery," Journal of Vascular and Interventional Radiology, vol. 12, No. 4, pp. 497-499, Apr. 2001.

Murphy et al., "Use of a Curved Needle for True Lumen Re-entry during Subintimal Iliac Artery Revascularization," Jouranl of Vascular and Interventional Radiology, vol. 8, No. 4, pp. 633-636, Jul.-Aug. 1997.

Nasim et al., "Intentional Extraluminal Recanalisation of the Femoropopliteal Segment Following Perforation During Percutaneous Transluminal Angioplasty," European Journal of Vascular and Endovascular Surgery, vol. 12, pp. 246-249, 1996.

Nydahl et al., "Subintimal Angioplasty of Infrapopliteal Occlusions in Critically Ischaemic Limbs," European Journal of Vascular and Endovascular Surgery, vol. 14, pp. 212-216, 1997.

Office Action issued for U.S. Appl. No. 13/229,378 on Sep. 6, 2013, 10 pages.

Office Action issued in U.S. Appl. No. 13/229,392 on Nov. 7, 2013, 10 pages.

Reekers et al., "Percutaneous intentional extraluminal (subintimal) recanalization: How to do it yourself," European Journal of Radiology, vol. 28, pp. 192-198, 1998.

Reekers et al., "Percutaneous Intentional Extraluminal Recanalisation of the Femoropopliteal Artery," European Journal of Vascular Surgery, vol. 8, pp. 723-728, 1994.

Won et al., "Microcatheter Placement through a Side Hole Created in a 5-F Catheter into Proximal Subclavian Arterial Branches Causing Hemoptysis," Journal of Vascular and Interventional Radiology, vol. 15, No. 8, pp. 881-884, Aug. 2004.

U.S. Appl. No. 15/227,800 entitled Reentry Catheter and Method Thereof, filed Aug. 3, 2016.

* cited by examiner

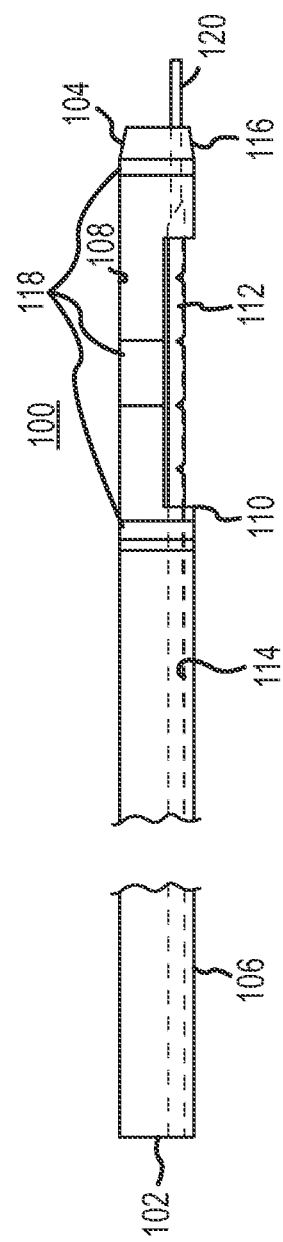

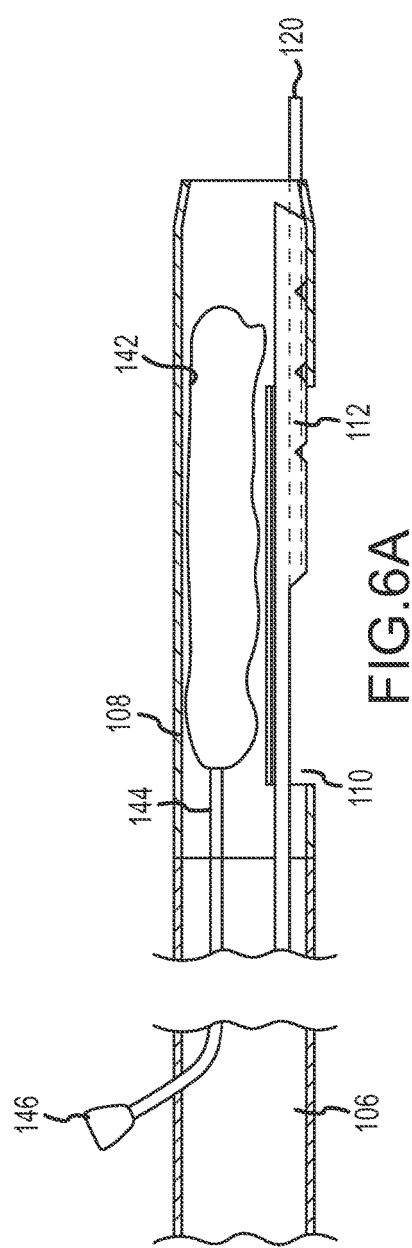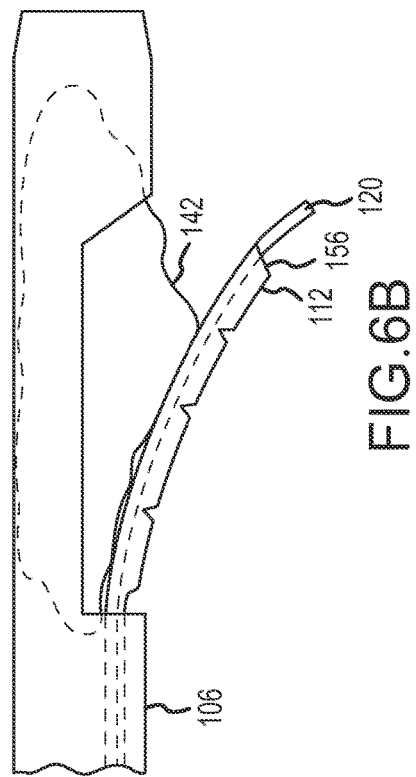

REENTRY CATHETER AND METHOD THEREOF

CROSS-REFERENCE TO RELATED APPLICATIONS

This application is a continuation of U.S. patent application Ser. No. 13/229,392, filed Sep. 9, 2011, which claims the benefit of U.S. Provisional Patent Application No. 61/503,477, filed on Jun. 30, 2011. The above applications are hereby incorporated by reference for all purposes as if fully set forth herein.

FIELD OF THE INVENTION

The invention generally relates to method and apparatus for crossing an obstruction in a tubular member, and more particularly to a medical device method for crossing of a chronic occlusion in a subintimal or interstitial space of an artery.

BACKGROUND OF THE INVENTION

Atherosclerosis is a common human ailment arising from deposition of fatty-like substance, such as atheroma, or plaque on the walls of major blood vessels. These deposits occur within the peripheral arterial system which feeds the limbs of the body and also occur within the coronary arterial system which feeds the heart. These deposits accumulate in localized areas, narrow the vascular lumen, and eventually causing restriction of normal blood flow. In some cases, the deposits result in a chronic partial or total occlusion. Such restriction can lead to a serious health risk including critical limb ischaemia. If blood flow cannot be adequately restored through surgical or endovascular intervention and the probability of limb amputation increases dramatically.

Until recently, chronic total occlusions have been treated by bypass which poses high procedural risks and is quite traumatic to the patient. Recently, catheter based intravascular procedures have been utilized. These techniques include step-by-step crossing of an occlusion using Excimer laser atherectomy devices and methods, crossing the occlusion with highly flexible and maneuverable guide wires, and other techniques known in the art. Once the lesion has been crossed, then standard endovascular devices such as laser atherectomy, angioplasty, stenting, and the like, can be used to enlarge the lumen and increase blood flow within the peripheral arterial system. These catheter-based intravascular procedures are typically preferred since they are much less traumatic to the patient, safer and cost-effective while delivering comparable long term vessel patency compared to more traumatic surgical alternatives.

Before catheter-based treatments can be used, with the exception of step-by-step Excimer laser methods, the guide wire must first pass through the total occlusion to provide access for the interventional catheter. Specifically, once a guide wire has crossed the occlusion, it can then be used as a rail to support interventional catheters. In some cases, the physician can maneuver the guide wire through the total occlusion establishing access. In many instances, the physician encounters a calcified cap on the proximal end of the occlusion and is unable to maneuver the guide wire through the cap and across a calcified or fibrous lesion. In many cases, the guide wire inadvertently penetrates the subintimal space between the intimal layer and the adventitial layer of the blood vessel as the guide wire attempts to cross the lesion. Once in the subintimal space, it is difficult to direct the guide wire back into the vessel lumen making it nearly impossible to perform a catheter based intravascular procedure.

In one related art technique, Dr. Bolia developed a revasculature procedure as described in *Recanalisation of femoropopliteal occlusions: Improving success rate by subintimal recanalisation*, Clinic Radiol, 40:325, 1989, by exploiting the subintimal space where a guidewire enters the subintimal space between the intima and adventitia layers, is subsequently advanced to a point distal to the occlusion, and then maneuvered to re-enter or puncture the vessel layers to enter the true lumen of the vessel. Once the guide wire has traversed through the subintimal layer and re-enters the true lumen of the vessel at a point distal to the occlusion, percutaneous balloon angioplasty is performed to restore blood flow through subintimal recanalization. This is a highly skilled technique with a low to moderate success level of consistent re-entry at the physician's preferred location just distal to the occlusion.

There are number of other related art catheters and methods for forming lateral penetrations through tissue to and from blood vessels past total occlusions, some of these are described in U.S. Pat. Nos. 5,443,497; 5,429,497; 5,409,019; 5,287,861; 6,231,546; 6,217,527; 6,506,178; 6,221,049; 6,235,000; 6,511,458; 6,719,725; 7,004,173; and 7,179,270, all of which are incorporated by reference for teaching reentry catheters, methods and for the purpose of written description and enablement requirements. These related art methods embody penetration of a needle exiting through either a side port or through a distal port, the needle must be oriented properly to ensure that the needle, when deployed, re-enters at a preferred location distal to the occlusion. One problem with these methods is a tendency of the catheter to back out as a result of the moment imposed by force required to penetrate the subintimal layers to gain access to the vessel true lumen. This is particularly problematic in the presence of calcified lesions causing an increase in the forces necessary for successful re-entry and, in many cases, requiring the physician to re-enter at a sub-optimal location.

SUMMARY OF THE INVENTION

The invention is directed to a medical device and method thereof that substantially obviates one or more of the problems due to limitations and disadvantages of the related art.

An advantage of the invention is the reduction in the forces required to cross the subintimal layer during device reentry into the true vessel lumen due to the articulating cannula or sharp member.

Yet another advantage of the invention is the reduction in the overall required size of the device since a long rigid element is not needed at the distal tip to support large reentry forces.

Still another advantage of the invention is improved stability and control of the distal tip during deployment of the cannula or interventional wire upon reentry from the subintimal space to the true vessel lumen thereby preventing against the device backing out or further separating the intima from the adventitia.

Yet another advantage of the invention is improved trackability and control, thereby allowing a physician or operator to re-enter the true vessel lumen at their preferred location close to the distal end of the total occlusion.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, is to provide a method for crossing an obstruction in a blood vessel. The method includes advancing a guide wire into an interstitial space of a vessel. Next, a catheter is advanced into the subintimal space with the aid of the guide wire. This may be accomplished using a traditional over the wire approach or using a rapid exchange catheter. For example, a rapid exchange reentry catheter method and catheter is described in U.S. Patent Application No. 61/503,477, which is hereby incorporated by reference as if fully set forth herein.

In one embodiment, a second wire or the original wire in an over the wire configuration, is advanced down a central lumen of a reentry member that is configured to deploy through at least one distal port to gain access to a vessel true lumen from a subintimal space.

In a preferred embodiment, the operator activates the reentry member through either a push or pull mechanism or the deployment of a balloon to direct the sharp from the subintimal space into the vessel lumen. Through this preferred embodiment, reentry into the true lumen of a vessel is accomplished at a location immediately distal to the total occlusion. It is noted that other locations may also be used for reentry. Preferably, the reentry member is configured to exit the lateral port and into the true lumen of the vessel from the subintimal space prior to advancement of an intervention wire through the lateral port.

Another aspect of the invention is directed towards a catheter system that includes a catheter having a proximal end, a distal end, lateral port, and at least one lumen. At least one lumen extends longitudinally through at least the lateral port of the catheter. The catheter includes a reentry member which is configured to gain access to a vessel true lumen from a subintimal space. The reentry member is configured to penetrate the vessel layers adjacent to the distal port. In a preferred embodiment, the reentry member has one or more sharpened edge surfaces along a distal portion of the cutting device. The reentry member is configured to have a hollow portion to receive an interventional guide wire.

Yet another aspect of the invention is directed towards a reentry catheter for use in forming a pathway in an interstitial space of an artery. The reentry catheter includes a catheter body including a proximal end, a distal end, at least one lumen, and at least one port. An exchange port is arranged on at least a distal portion of the catheter body and the exchange port includes at least one lumen configured to receive a guidewire and the catheter body is configured to track over the guidewire to a treatment site. A reentry member is slidably arranged within the lumen of the catheter body and is configured to deploy through the catheter body port. In one embodiment, the reentry member is configured to deploy from a first location within the interstitial space of an artery to a second location within a true lumen of the artery upon application of a substantially eccentric force to a distal portion of the reentry member.

Still yet another aspect of the invention is directed towards a reentry catheter for use in forming a pathway in an interstitial space of an artery. The reentry catheter includes a catheter body having a proximal end, a distal end, at least one lumen, and at least one port. An exchange port is arranged on at least distal portion of the catheter body. The exchange port is configured to receive a guidewire and the catheter body is configured to track over the guidewire to a treatment site. A reentry member having a proximal end, a distal end, at least one lumen is configured to be slidably positioned within the lumen of the catheter body. The reentry member includes a portion having a sharp surface to permit dissection of a portion of an artery. A tether is coupled to a distal end portion of the reentry member and the reentry member is configured to deploy through the at least one port from a first location within the interstitial space of an artery to a second location within a true lumen of the artery upon application of a force to the tether.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 illustrates an exemplary side view of a reentry catheter according to an embodiment of the invention;

FIGS. 6A-6B illustrate a mechanism for controlling a reentry member according to another embodiment;

DETAILED DESCRIPTION OF THE ILLUSTRATED EMBODIMENTS

Figure 2A:
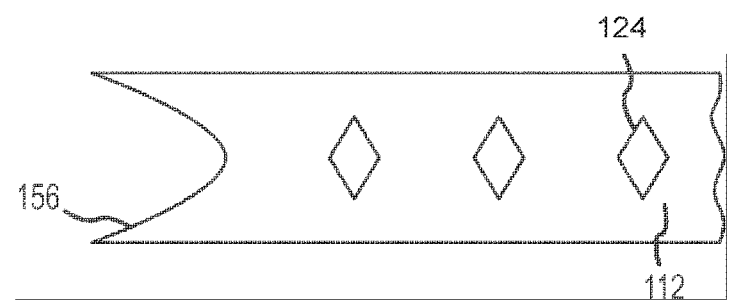
FIG. 2A illustrates an exemplary bottom-profile view of the reentry member illustrated in FIG. 1.

The invention generally relates to a method and system for crossing an obstruction in a tubular member, e.g., crossing a chronic total occlusions in a blood vessel, and more particularly to a medical device method for crossing of an occlusion in a subintimal or interstitial space of an artery. Subintimal or interstitial region or space is at a location beneath at least a portion of intima and preferably at a location contained between the intima and the adventitia of the vessel. The terms tubular member, artery, vessel and bodily passable are used interchangeably throughout the specification.

An embodiment of invention is directed towards a catheter for insertion into a subintimal space. The catheter includes a proximal end, a distal end, at least one lateral port, and at least one lumen for receiving a guide wire. The at least one lumen extends longitudinally through at least the lateral port of the catheter. The catheter may also include an exchange port, e.g., RX port, arranged along an exterior portion of the catheter body and configured to receive a second wire or guide wire. The exchange port may be broken into two or more segments along the length of the catheter.

The catheter also includes a reentry member including at least one sharp surface and configured to operate out of a portion of the lateral port. In one embodiment, the reentry member is configured with one or more sharp surfaces near its distal end, e.g., in a tear drop cross-section configuration. Alternatively, the cutting surface may extend along the entire surface of the reentry member or only a predetermined portion. Preferably, the cutting surface is configured to gain access from the subintimal or interstitial region or space to the true lumen of the vessel. In one embodiment, the reentry member includes a lumen for receiving a guide wire or supplemental treatment device. These supplemental treatment devices may include guide wires, medical instruments, balloons, stents, laser catheters, optical fibers, visualization devices, medications and other medical instruments known in the art. In a preferred embodiment, the lumen portion of the reentry member is configured to receive a guide wire having a diameter in a range from about 0.01 inches to about 0.04 inches or larger.

In one embodiment, a catheter system includes a catheter body having a proximal end, a distal end, and at least one lumen wherein the lumen includes a lateral opening. A reentry member including at least one void space or cut out that enables flexing is formed in at least a distal portion of the reentry member. The reentry member is configured to flex from a first a position to a second position upon application of a force to a distal region of the reentry member.

In another embodiment, a reentry catheter for use in forming a pathway in an interstitial space of an artery includes a catheter body including a proximal end, a distal end, at least one lumen, and at least one port. An exchange port is arranged on at least a distal portion of the catheter body. The exchange port includes at least one lumen configured to receive a guidewire and the catheter body is configured to track over the guidewire to a treatment site. A reentry member includes a proximal end and a distal end where distal end of the reentry member is configured to deploy through the at least one port from a first location within the interstitial space of an artery to a second location within a true lumen of the artery upon application of a substantially eccentric force to a distal portion of the reentry member.

Another embodiment is directed towards a reentry catheter for use in forming a pathway in an interstitial space of an artery. The reentry catheter includes a catheter body having a proximal end, a distal end, at least one lumen, and at least one port. An exchange port is arranged on at least distal portion of the catheter body. The exchange port includes at least one lumen configured to receive a guidewire and the catheter body is configured to track over the guidewire to a treatment site. The reentry member includes a proximal end, a distal end, at least one lumen extending from the proximal end to the distal end. A tether or flexible tension member is coupled to a distal end portion of the reentry member. The tether is configured to deploy at least a portion of the reentry member through the at least one port from a first location within the interstitial space of an artery to a second location within a true lumen of the artery upon application of a force to the tether Suitable materials for the reentry member include but are not limited to steel, alloys, nitinol, titanium, thermoplastics, including PEEK or polyimide, and combinations thereof and the like. The reentry member may also be configured to have a predetermined shape, i.e., resilient shape, straight shape, curved shaped, memory shape, and combinations thereof.

In one embodiment, the reentry member is moveable, flexible and/or bendable from first configuration to a second configuration, e.g., a retracted position to an operative position. The movement may be achieved upon application of a force, e.g., an eccentric force applied to a portion of the reentry member. In some embodiments, the force may be generated with at least one of a tether; a control wire; a guide wire with a hook; push member; pull member; ramp; wedge; balloon; electrically activated materials, including electro-active polymers, thermo-active polymers, electroactive metals and combinations thereof.

The electrically activated materials may be activated with an electrical signal such as current or voltage as known in the art. For example, the catheter body or the reentry member may be constructed as described in U.S. Pat. No. 7,951,186, which is hereby incorporated by reference.

In other embodiments, at least a portion of the reentry member may have a load or force built into the member. For example, the reentry member may have pre-resilient shape and contained within a shroud or other structure that prevents movement. After the shroud or other structure is removed, the reentry member is released from a first position to second position.

The catheter may be constructed from various materials as known in the art. For example, the catheter may be constructed from materials, such as polyesters; polyurethanes; polyamides; polyolefins including polyethylene and polypropylene; and any copolymers thereof. Some more specific examples of suitable materials include, but are not limited to: nylon; polyester elastomer; polyether/block polyamide, such as PEBAX, Hytrel, and/or Amitel; polyamide such as Grilamid; fluoro-polymer, such as Kynar; polyether ether ketone (PEEK); polyethylene (PE); polyurethane; polyolefin copolymer (POC); tetrafluoroethylenes, such as polytetrafluoroethylene (PTFE).

Other suitable materials include steel, including laser cut stainless steel. The catheter may comprise coils as described in FIG. 9C as described in paragraphs [0101] and [0102] of U.S. Publication No. 2010/0063534, which is hereby incorporated by reference as if fully set forth herein. The catheter may comprise at least one lumen that is configured to allow supplemental treatment devices access to the interior of the lumen.

Another embodiment of the invention is directed towards a method for crossing an obstruction in blood vessel. The method includes advancing a first guide wire through a true lumen of vessel and into an interstitial space of the vessel. In some instances with severe calcification present, an undersized low profile balloon or other intervention dilation device may be used to pre-dilate the subintimal space prior to introduction of the reentry catheter. Next, the reentry catheter is advanced into the subintimal space through either an over the wire or via a rapid exchange technique with the reentry member in a stowed position. The catheter then advances through the subintimal space until the lateral port is distal to the total occlusion.

The orientation and the location of the catheter and its lateral port with respect to the occlusion may be directed through the use of radiopaque markers and visualization techniques known in the art. Once the catheter has been properly oriented, the operator moves the reentry member from the stowed or locked position and subsequently articulates the member such that a precise incision is made between the subintimal space and the true vessel lumen. A second interventional guide wire, in the case of a rapid exchange catheter, or the first guide wire for an over the wire configuration is advanced into the vessel lumen through the hollow portion of the reentry member. Once the intervention wire is in place, the reentry member may be retracted and the entire reentry catheter removed. Of course, more than one wire may also be used in the over the wire technique.

Yet another embodiment of the invention is directed towards a kit. The kit includes a catheter according to embodiments of the invention and optionally directions for use. The kit may also include a supplemental treatment device, e.g., a balloon, optical catheter, visualization catheter, stent, embolic protection device and the like. In addition, the kit may include valves and other devices that may be used in medical procedures.

FIG. 1 illustrates an exemplary side view of a reentry catheter according to an embodiment of the invention.

Referring to FIG. 1, a reentry catheter according to this embodiment is generally depicted as reference number 100. The catheter 100 is configured to permit a user to cross an obstruction, e.g., partial or total occlusion, in a subintimal space of a vessel. The catheter 100 also enables fast and simple true lumen reentry without the need for active visualization, e.g., IVUS visualization. Visualization may be used to assist procedures of the invention, e.g., the visualization may be active or passive. In one embodiment, visualization features are added as described with reference towards U.S. Patent Application Publication No. 2005/0171478, which is hereby incorporated by reference.

The catheter 100 is flexible and has a proximal end 102 and a distal end 104. The proximal end 102 is attached to a handle (not shown). A shaft 106 extends from the proximal end 102 of the catheter to the distal end of a rigid shroud or cover 108. The shaft 106 may be constructed of conventional techniques. In a preferred embodiment, the shaft includes braided, double braided, or by triplex construction as described in U.S. Patent Application No. 61/503,477, which is hereby incorporated by reference. A lateral port 110 is located near the distal end 104 and preferably in the rigid shroud 108. Alternatively, or in addition to, a lateral port (not shown) may also be located in the shaft 106. The shaft 106 includes at least one lumen 114 extending at least partially along the entire shaft 106 and exiting out the catheter distal end 104. In some embodiments, the lumen 114 may be used to provide supplemental treatment devices to the distal tip of the catheter 100.

The distal end of shaft 106 is connected to the proximal end of shroud 108 preferably by a laser weld, glue, over-molding or the like as known in the art. There may be more than one lateral port at a distal portion of the shroud 108.

Optionally, a flexible atraumatic tip 116 may be attached to the distal end of the shroud 108 preferably by a laser weld, glue, over-molding or the like as known in the art. Alternatively, the shroud or cover 108 may extend to the catheter distal end 104 and be formed with an atraumatic tip profile. Further, an over molded distal extension (not shown) of the catheter may be incorporated to provide additional support during device orientation and during launch of the reentry member 112. The reentry member 112 is docked in a straight position, as shown in FIG. 1 while traversing through an artery and into or reversed out of the subintimal vessel space. Alternatively, a retractable shroud or cover (not shown) may be used to protect the vessel during catheter transport through the body.

At least one marker, e.g., a radiopaque marker, 118 is disposed on the body of the catheter near its distal end or integrated within the body of the catheter. The radiopaque marker 118 is used with standard visualization techniques, e.g. fluoroscopy, to guide the catheter through the body and into position in the subintimal space, to position the lateral port 110 and reentry member 112 at a desired location distal to the occlusion, and to determine whether the reentry member 12 is in the stowed, ready, or in a fully articulated position. Radiopaque markers as described in U.S. Patent Application No. 61/503,477, U.S. Patent Application 2010/0317973, U.S. Pat. No. 6,544,230, U.S. Pat. No. 6,719,725, or U.S. Pat. No. 6,231,546 may also be used, which are hereby incorporated by reference as if fully set forth herein.

The reentry member 112 may be configured to permit other devices or supplemental devices to be operated through the lumen of the member 112. The supplemental devices may include a balloon, a cutting device, thrombectomy device, a guide wire, a filters, e.g., an embolic filter, optical devices, e.g., RF or laser ablation devices, combinations and the like. In addition, the reentry member 112 may be configured to have a predetermined shape, i.e., pre-resilient shape, straight shape, curved shaped, memory shape.

In a preferred embodiment, the lumen of the reentry member 112 is sized to accommodate a wide range of guide wire diameters such as guide wire diameters in a range from about 0.01 inches to about 0.04 inches or larger. Referring to FIG. 1, guide wire 120 is shown passing through a lumen of the reentry member 112 in its stowed position and passing through the distal end 104 of the catheter as would be the case when the catheter travels through the body and into or out of the subintimal space.

Figures 2B, 2C:
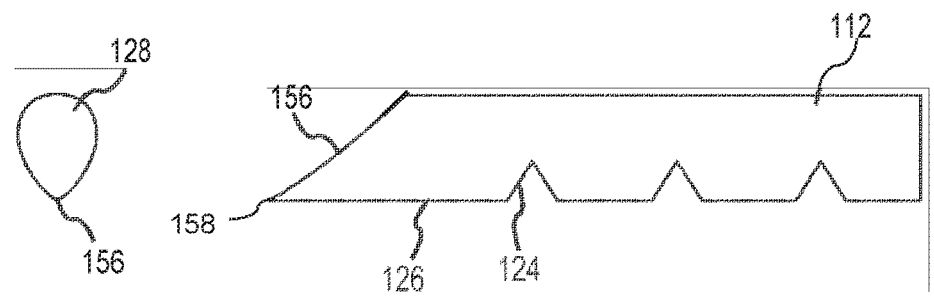
FIG. 2B illustrates an exemplary side-view of the reentry member illustrated in FIG. 1.
FIG. 2C illustrates an exemplary end-view of the reentry member illustrated in FIG. 1.

FIG. 2A illustrates an exemplary bottom-profile view of the reentry member illustrated in FIG. 1. FIG. 2B illustrates an exemplary side-view of the reentry member illustrated in FIG. 1. FIG. 2C illustrates an exemplary end-view of the reentry member illustrated in FIG. 1.

Referring to FIGS. 2A-2C, reentry member 112 is constructed with at least one void or cut geometry 124 that enables flexing. For example, when a force is placed at a distal region of the reentry member flexing or deflection of the distal region of the reentry may be achieved. In this embodiment, a diamond pattern 124 along the axis of the reentry member 112 is formed at least along a distal region of the reentry member 112. Though a diamond shape is illustrated in FIG. 2A, it is understood that the diamond shape may be any suitable geometric shape or combination of different geometric shapes, e.g., squares, triangles, rectangles, ovals, circles, hexagons, octagons, pentagons, and combinations thereof. Furthermore, the cut geometry 124 may be spaced at different distances along the reentry member 112 and the number of cut geometries 124 along the articulating cutting device may be varied. As more cut geometry 124 are used, it is easier to flex the reentry member 112 upon application of a force.

At least one portion of the bottom distal edge of the reentry member 112 is formed with a sharp leading edge 126. The reentry member 112 is hollow with a lumen 128 that is continuous with catheter lumen 114. The cut out or void 124 may also be spaced at various locations around the circumference of the reentry member 112 relative to a leading edge 126, e.g., about 2 degrees to about 180 degrees. In a preferred embodiment, the center of the cut out or void 124 is about 180 degrees relative to a leading edge 126. A sharp edge 156 at distal tip 158 of the reentry member 112 may also be utilized in this embodiment.

Figure 3A:
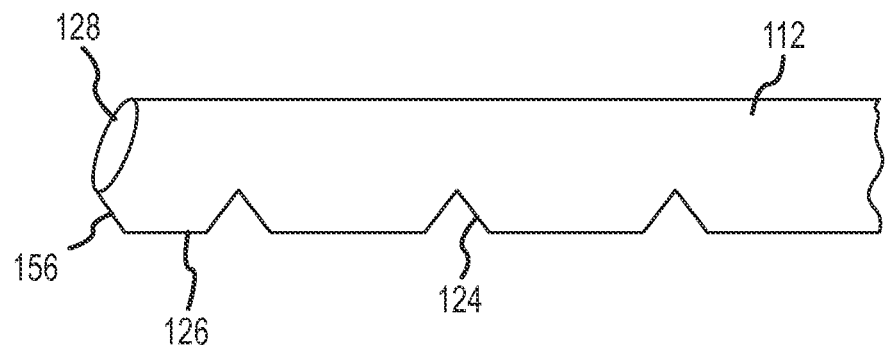
FIG. 3A illustrates an exemplary side view of the reentry member according to another embodiment of the invention.
Figure 3B:
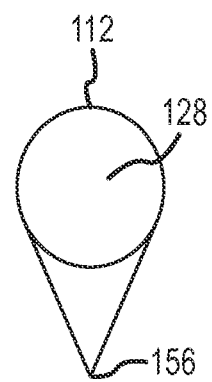
FIG. 3B illustrates an exemplary end view of the reentry member according to FIG. 3A.

FIG. 3A illustrates an exemplary side view of the articulating cutting device according to another embodiment of the invention. FIG. 3B illustrates an exemplary end view of the articulating cutting device according to FIG. 3A.

Referring to FIGS. 3A-3B, the reentry member 112 in this embodiment includes a shaft or hollow tube with a bottom edge profile. The bottom edge profile may also contain void or cutout geometry 124 to provide flex or curvature during device reentry. At least a portion of the bottom distal edge of the reentry member 112 is formed with a sharp leading edge 126. The reentry member 112 is hollow with a circular lumen 128 that is continuous with catheter lumen. An additional sharp edge 156 is arranged at distal tip of the reentry member 112.

Figure 4A:
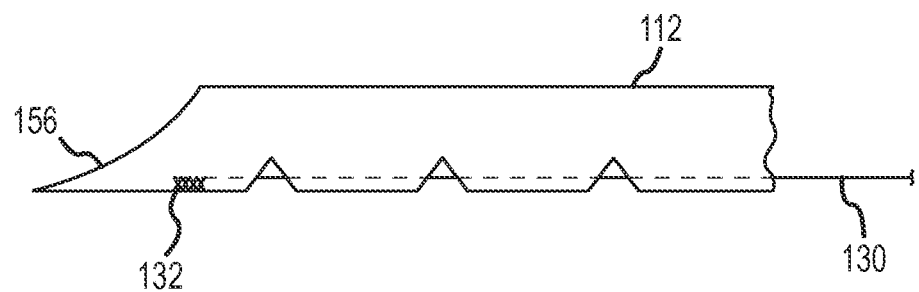
FIGS. 4A-4B illustrate a mechanism for controlling a reentry member according to another embodiment of the invention.
Figure 4B:
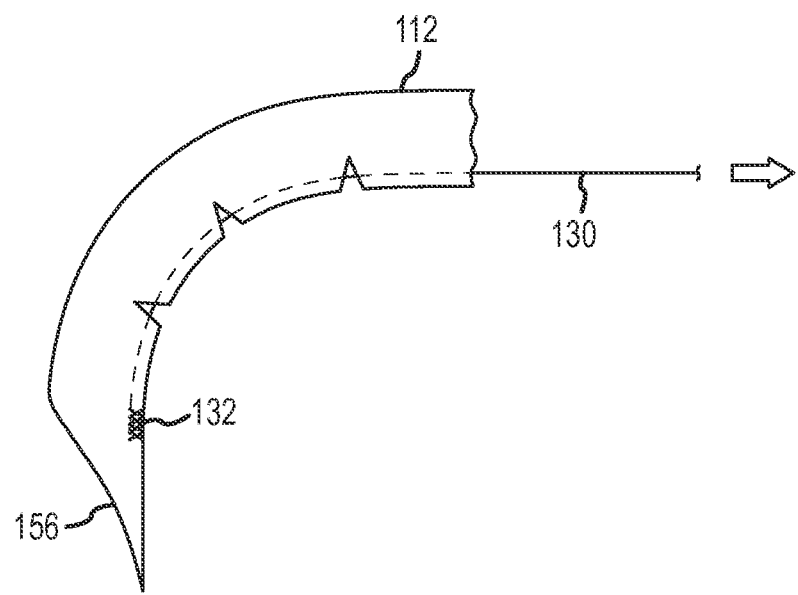

FIG. 4A illustrates a mechanism for controlling the reentry member according to another embodiment of the invention. FIG. 4B illustrates a mechanism of FIG. 4A for controlling the reentry member.

Referring to FIGS. 4A and 4B, a control wire 130 is coupled at an end region 132 of the reentry member 112 along an axis eccentric to the longitudinal axis of the device. In this embodiment, the control wire 130 is coupled to an inside surface of the reentry member 112. The control wire 130 may be coupled to the reentry member by any suitable technique, including but not limited to bonding, welding, mechanically coupled or combinations thereof.

In another embodiment, the control wire 130 may be the guide wire 120 configured to attach to distal portion of the reentry member 112, for example with a hook on the end of the guide wire 120.

During reentry, an operator would mechanically control the reentry member 112 by holding the catheter 100 in place and by pulling the control wire 130 as shown with the arrow in FIG. 4B. The control wire 130 is configured to transmit force from the proximal end of the catheter 100 to articulating or flexing at least a portion of the reentry member 112. The eccentric location of the control wire 130 and the placement of the coupled end 132 are such that a moment is created on the device causing it to move from a first position in FIG. 4A to a second position in FIG. 4B. This movement, bending or articulation is from an orientation of about parallel to the vessel wall to an orientation between about 0 and about 180 degrees of the vessel wall and more preferably between about 5 and about 90 degrees with respect to the vessel wall and allowing the sharp edge 126 to penetrate the vessel wall.

The control wire may be comprised of at least one tendon, tether, coil, cable, linkage and made of a suitably flexible material capable of withstanding a high tension load such as Kevlar, Nylon, Nitinol, biocompatible metal wire, or other material known in the art.

Figure 5A:
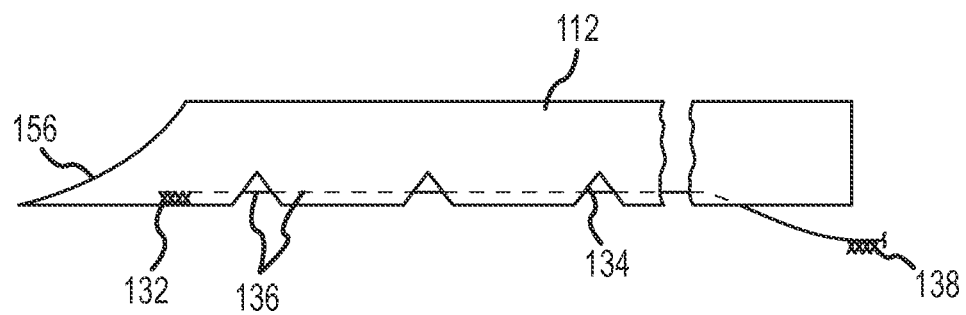
FIGS. 5A-5B illustrate a mechanism for controlling a reentry member according to another embodiment of the invention.
Figure 5B:
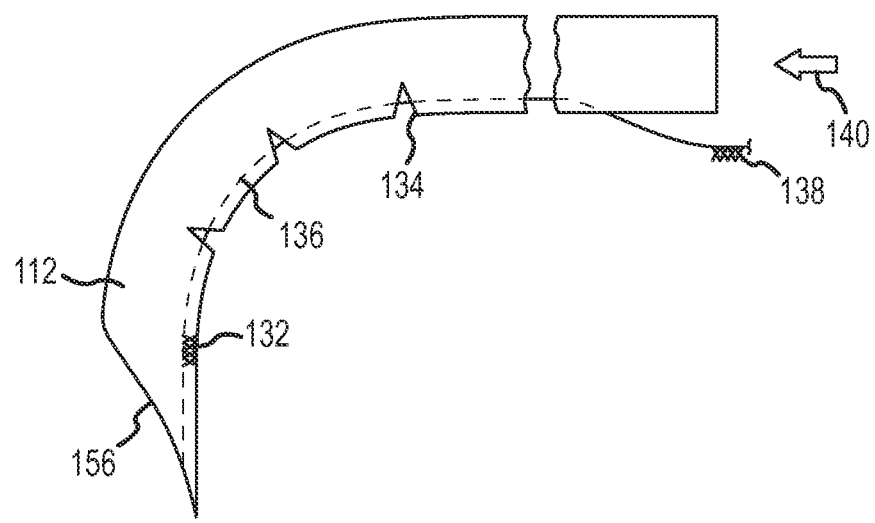

FIGS. 5A-5B illustrate a mechanism for controlling the articulating cutting device according to another embodiment of the invention.

Referring to FIGS. 5A-5B, a tether element 136 is coupled at a location 132 near the distal end of the reentry member 112 and the tether element 136 is coupled at proximal end of to the shroud 108 or catheter shaft 106 at a point proximal to the most proximal void or cut out 134.

During reentry, an operator would control the reentry member 112 by holding the catheter 100 in place and pushing the reentry member 112 in the direction of the arrow 140. The pushing force is configured to provide the necessary force to curve or flex the distal end of reentry member 112 from a first orientation, e.g., parallel to the vessel wall to a second orientation between about 0 and about 180 degrees of the vessel wall and more preferably between about 5 and about 90 degrees with respect to the vessel wall. Thereby, allowing a leading edge 156 of the reentry member 112 to penetrate the vessel wall and reenter a true lumen of the vessel. Alternatively the control wire 130 in FIG. 4 or the tether 136 in FIG. 5 may be comprised of a pull cable or mechanical linkage as known in the art. Optionally, mechanical advantage components such as levers, manual gearing or electro-mechanical gearing may be incorporated near the proximal end of the catheter and more preferably in the handle such that the reentry member 112 may be mechanically controlled through a simple one-handed operation. In a preferred embodiment, the tether element 136 includes a rigid linkage is coupled to the proximal end of the element and coupled to a translating actuator on a handle. Translational movement of the actuator would place the tether element in tension causing the reentry member to articulate through the lateral port. Alternatively, other actuating mechanisms such as knobs, and the like, as known in the art can be utilized.

FIGS. 6A-6B illustrate a mechanism for controlling the reentry member according to another embodiment of the invention.

Referring to FIGS. 6A-6B, the reentry member 112 is deployed with use of elastomeric device, e.g., a balloon, located inside the distal portion of the catheter near the lateral port 110. The reentry member 112 is shown in stowed position in FIG. 6A. In a preferred embodiment, a high pressure, non-compliant balloon 142 is locate in the distal end region of the reentry catheter 100, preferably within the rigid shroud 108, and above the lateral port opening 110 and the reentry member 112. An inflation lumen 144 is in fluid communication with the deployment balloon 142 and an inflation port 146 located along the shaft 106 at a location proximal to the rigid shroud 108 or at or near a proximal hub the catheter (not shown).

After inflation of the balloon 142 the reentry member 112 moves to a second position or a non-stowed position. More specifically, the non-compliant balloon 142 exerts an eccentric load on the top edge of the reentry member 112 to deliver the necessary force to curve or flex the distal portion of the reentry member 112 from an orientation about parallel to the vessel wall to an orientation between about 0 and about 180 degrees of the vessel wall and more preferably between about 5 and about 90 degrees with respect to the vessel wall.

After articulated to a predetermined position, the entire catheter body, if necessary, may be pulled proximally causing the intimal tissue to be forced against the sharp leading edge 156 creating a subintimal arteriotomy. This action may be controlled mechanically using the controls integrated in the proximal handle (not shown). The distal tip of the reentry member 112 would then be inside the true lumen of the vessel and a guide wire 120 or supplementary intervention device may be passed through the central lumen of the reentry member 112.

Figure 7:
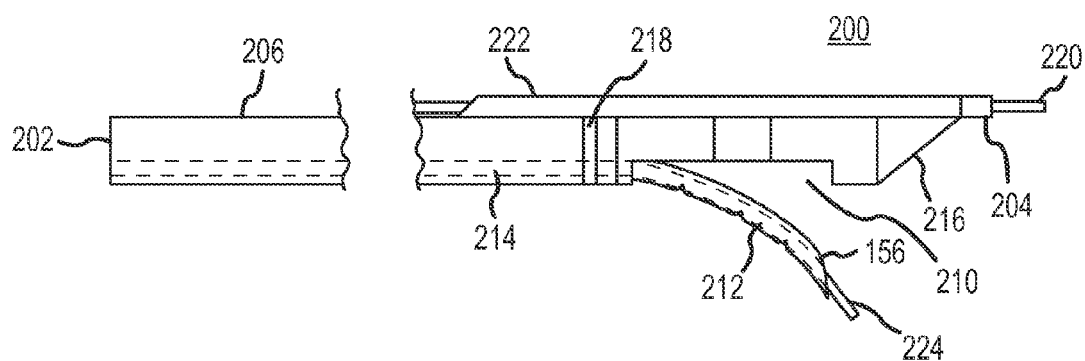
FIG. 7 illustrates an exemplary side view of a reentry catheter according to another embodiment of the invention.

FIG. 7 illustrates an exemplary side view of a reentry catheter according to another embodiment of the invention. Referring to FIG. 7, a reentry catheter according to this embodiment is generally depicted as reference number 200. An exchange port 222, e.g., rapid exchange port, is eccentrically located near the distal end of shaft 206. The exchange port 222 may include a jacketed polyimide tube trimmed flush to the profile of the device after processing to facilitate tracking and back loading of a first guide wire 220. The exchange port 222 may be sized to extend past a distal end of the catheter, be flush with the distal end of the catheter, or terminate a location proximal the distal end of the catheter. Preferably, the guide wire 220 may have a diameter in a range from about 0.01 inches to about 0.04 inches or greater and be constructed of a range of materials as known in the art. In addition, the wire 220 may have lubricous coating, e.g., PVP thin film or PTFE, and/or a predetermined shape. Additionally, the wire 220 may be removed allowing supplemental treatment devices access to the distal tip of the catheter. Additionally, the wire 220 may be removed allowing supplemental treatment devices access to the distal tip of the catheter. The supplemental treatment devices include but are not limited to, guide wires, medical instruments, balloons, stents, laser catheters, medications, optical catheters and other medical instruments known in the art.

The catheter 200 is flexible and has a proximal end 202 and a distal end 204. The proximal end 202 is attached to a handle (not shown). A shaft 206 extends from the proximal end 202 of the catheter to the distal end of a rigid shroud 208. The shaft 206 may be constructed of conventional techniques, e.g. braided or double braided, or by triplex construction as described herein. A lateral port 210 is located near the distal end and preferably in the rigid shroud 208. Alternatively, or in addition to, a lateral port (not shown) may also be located in the shaft 206. The shaft 206 includes a lumen 214 extending at least partially along the entire shaft 206.

A reentry member 212 may be contained in the inner lumen of shaft 206 along substantially the length of catheter 200. In some embodiments, the reentry member 212 is hollow and allows for an optional second guide wire, cannula or other supplemental treatment device 224. The distal end 204 of shaft 206 is connected to the proximal end of the shroud preferably by a laser weld, glue, over-molding or the like as known in the art. There may be more than one lateral port at a distal portion of the shroud. Optionally a flexible atraumatic tip 216 may be attached to the distal end of the shroud preferably by a laser weld, glue, over-molding or the like as known in the art. Alternatively, the shroud may extend to the catheter distal end 204 be formed with an atraumatic tip profile.

Further, an overmolded distal extension (not shown) of the catheter may be added to a distal end of the catheter 200 as described in U.S. Patent Application No. 61/503,477, which is hereby incorporated by reference as if fully set forth herein. The over molded distal extension is configured to provide additional support during device orientation and during launch of the reentry member 212. The reentry member 212 is docked in a straight position, while traversing through an artery and into or out of the subintimal vessel space. Alternatively, a retractable shroud cover (not shown) may be used to protect the vessel during catheter transport through the body. The reentry member 212 may be mechanically controlled through the use of a tension member, a tether member or a balloon as described herein. Optionally, an additional lumen may be contained within the catheter 200 that may be used for supplemental treatment devices.

The catheter 200 optionally may include at least one radiopaque marker 218. In a preferred embodiment, the radiopaque markers are configured to ensure orientation of the lateral port towards the true lumen of the vessel. The radiopaque markers may also be configured to determine a spatial relationship of other attributes of the catheter, e.g., the spatial location of the distal end of the catheter, confirmation of the stowed position of the reentry member, etc. In a preferred embodiment, at least one marker 218 is arranged near a distal portion of the catheter.

FIGS. 8A-8H illustrates an exemplary method for using a medical device of FIG. 1 and FIG. 7.

Figure 8A:
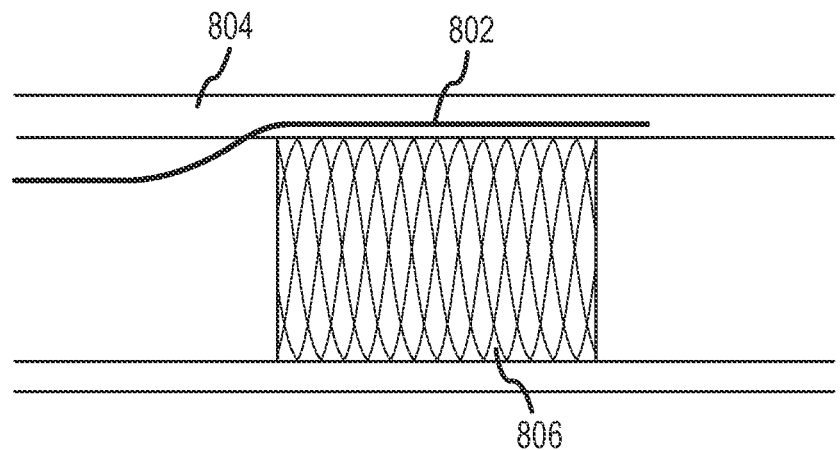
FIG. 8A-8H illustrates an exemplary method for using a medical device of FIG. 1 and FIG. 7.

Referring to FIGS. 8A-8E, a guide wire 802 is advanced to an occlusion 806 in an attempt by the physician to cross the occlusion 806 to use conventional interventional devices such as laser atherectomy catheters, balloons, drug delivery devices, stents and the like. This advancement of the guide wire 802 is done in accordance with techniques known in the field of cardiology, interventional radiology and the like. In some instances, the physician is unable to cross through the lesion from the proximal lesion end to a point distal the lesion through the true lumen of the vessel. In these instances, as shown in FIG. 8A, the guide wire 802 may unintentionally or intentionally enter the subintimal space 804 after reaching the total occlusion 806. The guide wire 802 may include lubricious coating and have diameter in a range from about 0.01 inches to about 0.04 inches or larger. In addition, the guide wire 802 may be shapeable, deformable, or have other attributes designed for crossing an occlusion 806 directly or indirectly.

Figure 8B:
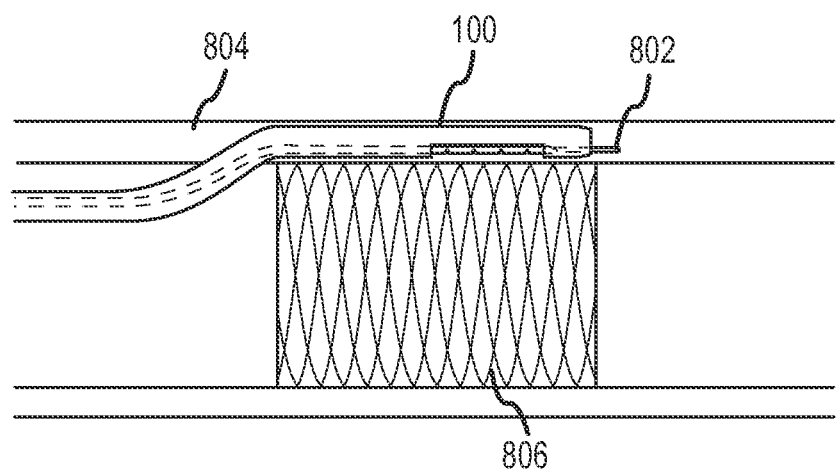

Referring to FIG. 8B, after the guide wire 802 has reached the subintimal space 804, a catheter 100 is advanced over the guide wire 802 into the subintimal space 804. Alternatively for the embodiment shown in FIG. 7, reentry catheter 200 would advance through RX port 222 into the subintimal space 804. Of course, any catheter described herein may also be used and reference to catheter 100 and 200 is done merely out of convenience. Next, the catheter 100 is advanced to a position distal of the occlusion 806.

Figure 8C:
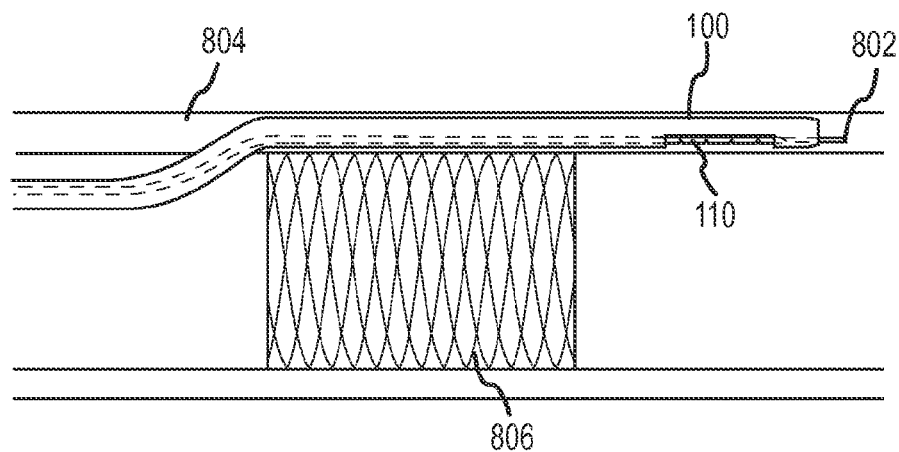

Referring to FIG. 8C, the catheter 100 is oriented to position such that the lateral port 110 is distal the occlusion 806. In a preferred embodiment, the orientation of the catheter 100 may be conducted with utilization of the radiopaque markers 118 as described previously and with reference to U.S. Patent Application No. 61/503,477, which is hereby incorporated by reference as if fully set forth herein. For example, in a preferred embodiment the catheter 100 is configured such that different views on fluoroscopic images enable the operator to align the lateral port 110 so that the reentry member 112 or other instrument, e.g., guide wire, working element, and the like, are aligned with a true lumen of the vessel. It is noted that other active or passive visualization techniques as known in the art may also be utilized to orient the lateral port 110 with a true lumen. Other visualization techniques may also be used to aid in orientation including incorporation of an active visualization element, such as an ultrasonic transducer or optical sensing element at a location either within the at least one catheter lumen, on or within the catheter body, or on or near the lateral port.

Figure 8D:
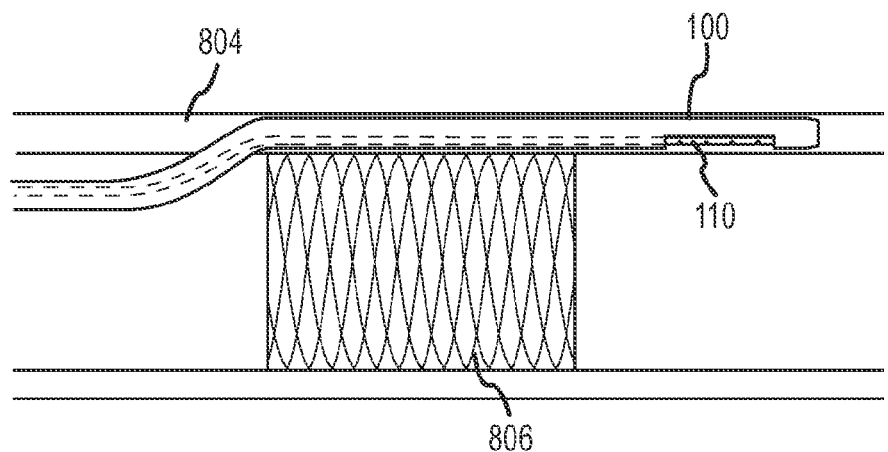
Figure 8E:
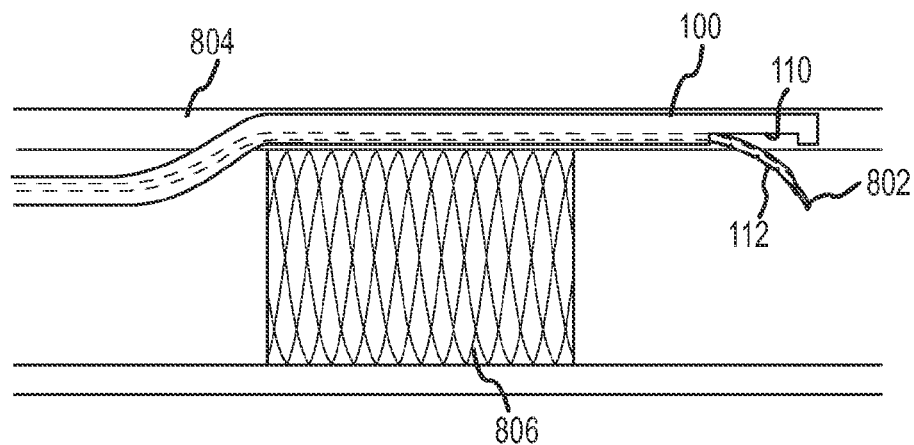

Once the catheter 100 is in position at a location distal to the occlusion 806 and the lateral port 110 and the reentry member 112 are oriented to articulate and launch into the true vessel lumen, the operator retracts the guide wire 802 to a position within the reentry member, as shown in FIG. 8D. The operator would then transition the reentry member 112 from a stowed, safe position, to a ready position in preparation for activation of the mechanical control for reentry. Alternatively this could involve retraction of a guard on the rigid shroud (not shown). Referring to FIG. 8E, reentry into the true vessel lumen is accomplished by the operator holding the catheter in place and articulating the reentry member 112 by either application of a tension load as described in FIGS. 4A-4B, a push mechanism as described in FIGS. 5A-5B or through inflation of an internal balloon as described in FIGS. 6A-6B. In the alternative or in addition to, the activation mechanism may be linked to a simple handle such that the operator either rotates a knob or activates a mechanical or electro-mechanical control element to transition from a ready to an articulated or flexed configuration. The intervention guide wire 802 or another appropriate device may be passed through the shaft lumen 114 and the lumen 128 of the reentry member 112 into the true vessel lumen.

Figure 8F:
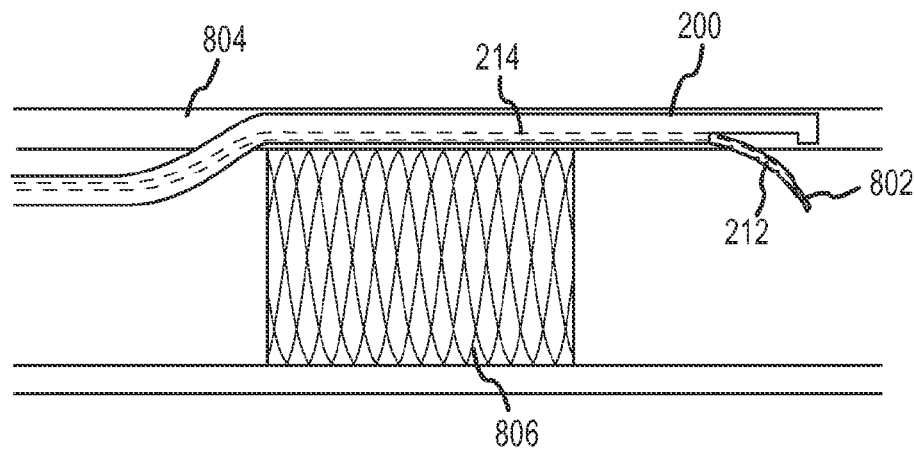
Figure 8G:
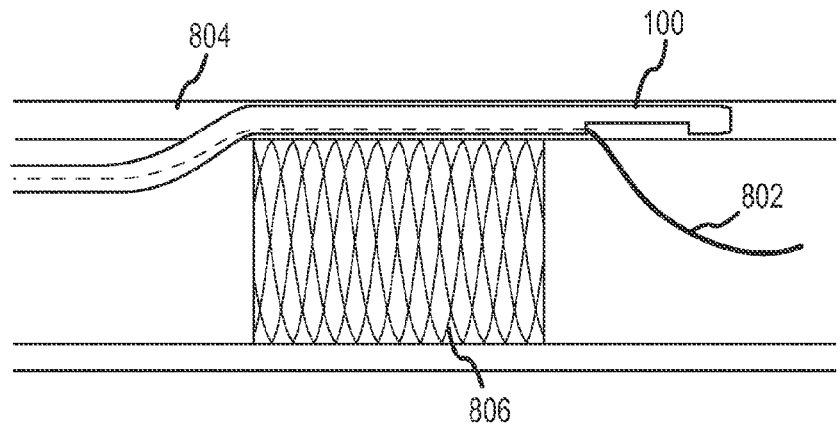

Alternatively for a rapid exchange configuration as described in FIG. 7 and FIG. 8F, retraction of guide wire 802 is not required. As with the previous embodiment, the operator would transition the reentry member 212 from a stowed, safe position, to a ready position in preparation for activation of the mechanical control for articulation. Alternatively this could involve retraction of a guard on the rigid shroud (not shown). Reentry into the true vessel lumen is accomplished by the operator holding the catheter 200 in place and articulating the reentry member 212 by techniques as described with regard to FIGS. 4A-4B, a push mechanism as described with regard to FIGS. 5A-5B or through inflation of an internal balloon as described with regard to FIGS. 6A-6B.

The activation mechanism may be linked to a simple handle (not shown) such that the operator either rotates a knob or activates a mechanical or electro-mechanical control element to transition from a ready to an articulated or flexed configuration. The guide wire 802 or another appropriate device may be passed through the shaft lumen 214 and the lumen of the reentry member 212 and into the true vessel lumen. The intervention guide wire may be sized from about 0.10 inches to about 0.40 inches or larger and may contain a lubricous coating as known in the art.

The reentry member 212 reenters the vessel lumen at an angle in a range from about 5 degrees to about 180 degrees, more preferably at an angle in range from about between about 5 degrees to about 90 degrees. The sharp edge 156 and/or 126 on the reentry member dissects the vessel wall from the subintimal space 804 into the true vessel lumen. The cutting action significantly reduces the force required to safely and accurately reenter the vessel lumen even in the presence of calcified tissue. This reentry force is significantly lower than the forces required for known reentry devices, which require lateral extension of the catheter and improved torsional control to support reentry forces. During reentry, the vessel wall tends to pull away from a more traditional reentry cannula tip during reentry such that penetration will require an increased force application and possible multiple attempts to successfully enter the lumen. The use of a reentry member overcomes this challenge posed by the prior art and allows the operator to reenter at their preferred location easily and repeatedly. Moreover, it is thought that the use of the reentry member results in more consistent reentry at a location closer to the distal point of the occlusion 806 as compared to the use of a simple curved cannula as known in the art.

Figure 8H:
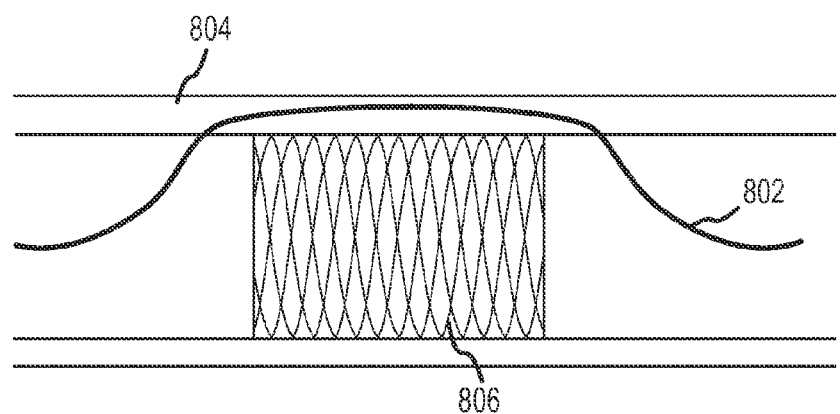

Referring to FIGS. 8E-8H, after the proper reentry of the reentry member 112 has been confirmed to be directed towards the true lumen of the vessel, another instrument, e.g., guide wire, working element, and the like, exits the lateral port 110 and reenters the vessel. Once the intervention guide wire or intervention device is in position, the reentry member is retracted back into the lateral port 110 of the catheter 100 and the catheter is removed as shown in FIG. 8H. Optionally, both the catheter 100 and guide wire 802 may be left in place. Now that the total occlusion 806 is crossed various interventional procedures as known in the art may be performed. For example, a balloon catheter (not shown) may be used to dilate the subintimal space along with possible stent placement (not shown) to provide an alternative lumen through the subintimal space 804 and back into the true vessel to restore adequate blood flow post-procedure.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A catheter system, comprising:
a catheter body having a proximal end, a distal end, at least one lumen running along a longitudinal axis from the proximal end through the distal end, and a lateral opening disposed on a periphery of the catheter body and in communication with the at least one lumen; and
a tubular reentry member comprising a distal end, the distal end comprising:
a first sharp edge parallel to the longitudinal axis to permit cutting, wherein the first sharp edge is formed on at least a portion of a bottom distal edge and extending outwardly from a surface of the tubular reentry member, wherein the bottom distal edge is parallel to the longitudinal axis, the bottom distal edge being opposite a top edge of the tubular reentry member;
a second sharp edge to permit cutting, wherein the second sharp edge and the first sharp edge meet at an angle and form a distal tip of the distal end of the tubular reentry member, wherein the angle is less than 90 degrees;
wherein the tubular reentry member is configured to flex from a first position inside the at least one lumen to a second position outside of the at least one lumen and through the lateral opening of the catheter body when an axial eccentric load is placed on the top edge of the tubular reentry member.

2. The catheter system of claim 1, wherein the axial eccentric load is applied with at least one of a control wire, a cabling device, a ramp, and an elastomeric member.

3. The catheter system of claim 1, wherein the reentry member comprises a material selected from the group consisting of an electroactive polymer, a thermo-active polymer, an electroactive metal and combinations thereof.

4. The catheter system of claim 3, wherein the axial eccentric load is applied with an electrical signal applied to the reentry member.

5. The catheter system of claim 1, wherein the reentry member comprises a pre-resilient shape.

6. The catheter system of claim 1, wherein the reentry member comprises a material selected from the group consisting of stainless steel, nitinol, alloy, titanium, thermoplastics, polyether ether ketone (PEEK), polyimide, and combinations thereof.

7. The catheter system of claim 1, wherein the catheter body further comprises a second lumen, wherein the second lumen is configured to receive a guide wire having a diameter in a range from about 0.01 inches to about 0.04 inches.

8. The catheter system of claim 1, wherein the catheter body comprises a material selected from the group consisting of a polyester, a polyurethane, a polyamide, a polyolefin, a polyethylene, a polypropylene, a nylon, a polyester elastomer, a polyether/block polyamide, a Hytrel, a fluoropolymer, a polyether ether ketone, a polyolefin copolymer, a tetrafluoroethylenes, a polytetrafluoroethylene, a steel, a laser cut stainless steel and combinations thereof.

9. The catheter system of claim 1, wherein the at least one lumen of the catheter body is configured to receive a supplemental treatment device.

10. The catheter system of claim 9, wherein the supplemental treatment device is selected from the group consisting of a guide wire, a medical instrument, a balloon, a stent, a laser catheter, a medication, an optical catheter and combinations thereof.

11. The catheter system of claim 1, further comprising at least one radiopaque marker arranged on a distal portion of at least one of the reentry member and the catheter body.

12. The catheter system of claim 1, wherein the reentry member further comprises at least one void space in a circumferential portion of the reentry member that is configured to enable flexing of the reentry member from the first position to the second position, and wherein the at least one void space is disposed along the longitudinal axis of the catheter body.

13. The catheter system of claim 12, wherein the at least one void space comprises a plurality of cut out sections.

14. The catheter system of claim 13, wherein the plurality of cut out sections comprise at least one of the following geometrical configurations: a tear drop configuration, a diamond configuration, a square configuration, a pentagon configuration, a hexagon configuration and combinations of the same.

15. The catheter system of claim 1, further comprising an exchange port arranged on at least a distal portion of the catheter body, wherein the exchange port comprises at least one lumen configured to receive a guidewire and the catheter body is configured to track over the guidewire to a treatment site.

16. A method of crossing an obstruction in a blood vessel, comprising the steps of:
advancing a first guide wire into a lumen of the vessel towards the obstruction in the vessel;
advancing the first guide wire into a subintimal space of the vessel to a location distal of the obstruction;
advancing a catheter having at least one lumen running along a longitudinal axis and comprising a tubular reentry member over the guide wire to a location where a port disposed on a periphery of the catheter is at a location distal of the obstruction, wherein the tubular reentry member comprises a distal end, the distal end comprising a first sharp edge parallel to the longitudinal axis formed on at least a portion of a bottom distal edge and extending outwardly from a surface of the tubular reentry member, wherein the bottom distal edge is parallel to the longitudinal axis, the bottom distal edge being opposite a top edge of the tubular reentry member, and a second sharp edge, wherein the second sharp edge and the first sharp edge meet at an angle and form a distal tip of the distal end of the tubular reentry member, wherein the angle is less than 90 degrees, the tubular reentry member being configured to flex from a first position inside the at least one lumen to a second position outside of the at least one lumen and through the port of the catheter when an axial eccentric load is placed on the top edge of the reentry member; and
cutting with at least one of the first sharp edge and the second sharp edge of the tubular reentry member from a first location within the subintimal space of the vessel through the port to a second location within a true lumen of the vessel.

17. The method of claim 16, further comprising the steps of:
returning the reentry member from the second location to the first location; and
removing the reentry member from the vessel.

18. The method of claim 16, wherein the cutting step comprises inflating an elastomeric member.

19. The method of claim 16, wherein the cutting step comprises applying a force to a control wire, cable, or tether element.

20. A catheter system, comprising:
a catheter body having a proximal end, a distal end, at least one lumen running from the proximal end through the distal end, and a lateral opening disposed on a periphery of the catheter body and in communication with the at least one lumen; and
a reentry member comprising a distal end, the distal end comprising:
a first sharp edge to permit cutting, wherein the first sharp edge is formed on at least a portion of a bottom distal edge of the reentry member, wherein the distal end of the reentry member comprises a tear drop shaped cross section tapering to form the first sharp edge;
a second sharp edge to permit cutting, wherein the second sharp edge is formed on a leading edge of the distal end of the reentry member;
wherein the reentry member is configured to flex from a first position inside the at least one lumen to a second position outside of the at least one lumen and through the lateral opening of the catheter body when an axial eccentric load is placed at a portion of the reentry member.

* * * * *

UNITED STATES PATENT AND TRADEMARK OFFICE
CERTIFICATE OF CORRECTION

PATENT NO. : 9,775,969 B2
APPLICATION NO. : 14/631592
DATED : October 3, 2017
INVENTOR(S) : Alvarez et al.

Page 1 of 2

It is certified that error appears in the above-identified patent and that said Letters Patent is hereby corrected as shown below:

On the Title Page

Page 3, item (56), under "OTHER PUBLICATIONS", in Column 2, Line 45, delete "Jouranl" and insert -- Journal --, therefor.

In the Drawings

In Fig. 2A, Sheet 2 of 11, delete " 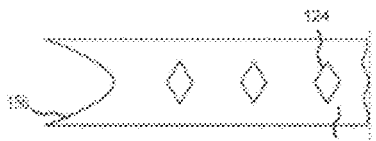 " and insert

-- 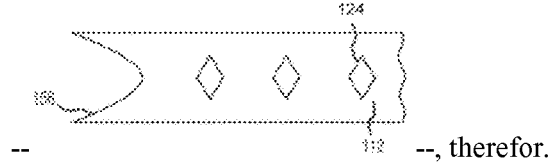 --, therefor.

In Fig. 2B, Sheet 2 of 11, delete " 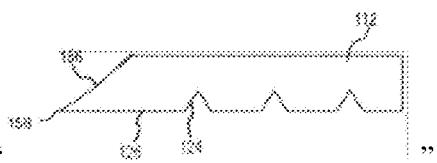 "

and insert -- 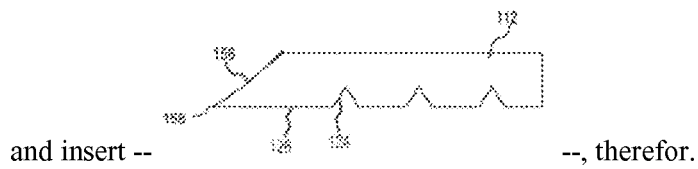 --, therefor.

Signed and Sealed this
Twenty-seventh Day of March, 2018

Andrei Iancu
*Director of the United States Patent and Trademark Office*

In Fig. 2C, Sheet 2 of 11, delete " 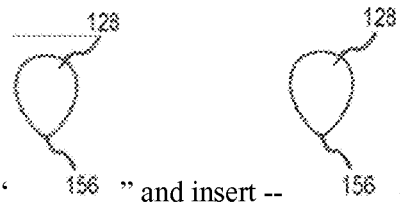 " and insert -- -- , therefor.

In the Specification

In Column 4, Line 47, delete "FIG. 8A-8H illustrates" and insert -- FIGS. 8A-8H illustrate --, therefor.

In Column 5, Line 67, delete "tether" and insert -- tether. --, therefor.

In Column 10, Line 28, delete "locate" and insert -- located --, therefor.

In Column 11, Line 34, delete "Optionally a" and insert -- Optionally, a --, therefor.

In Column 11, Line 66, delete "illustrates" and insert -- illustrate --, therefor.